United States Patent
Lo et al.

(10) Patent No.: US 9,458,422 B2
(45) Date of Patent: Oct. 4, 2016

(54) COMPOSITION OF MATTER AND METHOD FOR STIMULATING THE GROWTH OF BENEFICIAL MICROORGANISMS

(75) Inventors: Yangming Martin Lo, Ashton, MD (US); Irene N. N. Yossa, Silver Spring, MD (US); Neil A. Belson, Port Tobacco, MD (US)

(73) Assignees: University of Maryland, College Park, MD (US); Leaf Pro, LLC, Wilson, NC (US)

( * ) Notice: Subject to any disclaimer, the term of this patent is extended or adjusted under 35 U.S.C. 154(b) by 593 days.

(21) Appl. No.: 12/864,416

(22) PCT Filed: Jan. 26, 2009

(86) PCT No.: PCT/US2009/031995
§ 371 (c)(1),
(2), (4) Date: Nov. 2, 2010

(87) PCT Pub. No.: WO2009/094631
PCT Pub. Date: Jul. 30, 2009

(65) Prior Publication Data
US 2011/0053224 A1    Mar. 3, 2011

Related U.S. Application Data

(60) Provisional application No. 61/023,515, filed on Jan. 25, 2008, provisional application No. 61/106,426, filed on Oct. 17, 2008.

(51) Int. Cl.
*C12N 1/20* (2006.01)
*C12N 1/16* (2006.01)
*C12N 1/22* (2006.01)

(52) U.S. Cl.
CPC . *C12N 1/16* (2013.01); *C12N 1/20* (2013.01); *C12N 1/22* (2013.01); *Y02E 50/17* (2013.01)

(58) Field of Classification Search
None
See application file for complete search history.

(56) References Cited

U.S. PATENT DOCUMENTS 4,326,036 A    4/1982   Hayes et al.
2002/0137154 A1*  9/2002   Ingram et al. ............... 435/161
(Continued)

FOREIGN PATENT DOCUMENTS

WO    WO 2007100807    *  9/2007

OTHER PUBLICATIONS

Rao et al., "Antioxidative Activity of a Tobacco Leaf Protein Hydrolysates" Food Technology Biotechnology 45(1) 80-84 (2007).*

(Continued)

*Primary Examiner* — Blaine Lankford
*Assistant Examiner* — Lauren K Van Buren
(74) *Attorney, Agent, or Firm* — Nash and Titus, LLC

(57) ABSTRACT

The invention describes a novel composition of matter obtained from the leaves of green plants, which is useful in promoting the growth of beneficial microorganisms. Specifically, that the invention describes a hydrolysate prepared from plant leaf biomass (leaf biomass hydrolysate or 'LBH') which dramatically stimulates the growth of beneficial microorganisms. Use of LBH as a fermentation substrate can also stimulate rapid production of organic acids and other organic compounds. LBH can be used as a substrate to promote the fermentation-based production of biobased industrial chemicals or biofuels, LBH can be utilized as a prebiotic to promote the growth of beneficial probiotic organisms, hi addition, LBH may also be useful in stimulating the fermentation-based production of other products, examples of which include preservatives, antibiotics, antigens, vaccines, amino acids, vitamins, recombinant proteins, bioremediation treatments, and immobilized enzymes.

7 Claims, 7 Drawing Sheets

(56) References Cited

U.S. PATENT DOCUMENTS

| | | | |
|---|---|---|---|
| 2004/0161524 A1* | 8/2004 | Sakai et al. | 426/655 |
| 2006/0003448 A1* | 1/2006 | Fike et al. | 435/404 |
| 2006/0094104 A1* | 5/2006 | Grillberger et al. | 435/235.1 |
| 2007/0155000 A1 | 7/2007 | Nilsson et al. | |

OTHER PUBLICATIONS

Rao et al. "Antioxidative Activity of Tobacco Leaf Protein Hydrolysates" Food Technol. Biotechnol. 45(1) 80-84 (2007).*
Halliwell "Oxidative stress in cell culture: an under appreciated problem?" FEBS Letters 540 (2003) 3-6.*
USDA Grant Report (2006-2007) "Development of a Tobacco Biorefinery" Pharmacognetics Inc. Grant No. 2006-33610-16829.*
"Alternative Uses for Tobacco," U.S. Department of Agriculture, Cooperative State Research, Education, and Extension Servive Proposal (2004).*
"Development of a Tobacco Biorefinery" U.S. Department of Agriculture Small Business Innovation Research Phase I and Phase II Project Summary (2005).*
Guohua Rao et al., "Antioxidative Activity of Tobacco Leaf Protein Hydrolysates", Food Technol. Biotechnol, vol. 45, No. 1, pp. 80-84, (2007).
Yl-Chun Yeh et al., Effects of Chinese Wolfberry (*Lycium chinese* P.Mill.) Leaf Hydrolysates on the growth of Pediococcus acidilactici, Bioresource Technology, vol. 99, pp. 1383-1393, (2002).
Carlos Martin et al., "Preparation of Hydrolysates from Tobacco Stalks and Ethanolic Fermentation by *Saccharomyces cerevisiac*", World Journal of Microbiology & Biotechnology, vol. 18, pp. 857-862, (2002).
International Search Report dated Aug. 26, 2009, Application No. PCT/US2009/031995; filed Jan. 26, 2009.
"Development of a Tobacco Biorefinery", U.S. Department of Agriculture Small Buisiness Innovation Research Phase I and Phase II Project Summary (2005).
"Alternative Uses for Tobacco", U.S. Department of Agriculture, Cooperative State Research, Education, and Extension Service Proposal (2004).
Ezeji et al., "Butanol Production From Agricultural Residues: Impact of Degradation Products on *Clostridium beijerincki* Growth and Butanol Fermentation", *Biotechnology and Bioengineering*, vol. 97, No. 6 (2007) 1460-1469.
Saha et al., "A low-cost medium for mannitol production by *Lactobacillus intermedius* NRRL B-3693", *Appl. Microbiol. Biotechnol.* (2006) 72: 676-680.
Vasileva-Tonkova et al., "New Protein Hydrolysates from Collagen Wastes Used as Peptone for Bacterial Growth", *Current Microbiology*, vol. 54, pp. 54-57 (2007).
Altaf et al., "An Economic Approach for L-(+) lactic acid fermentation by *Lactobacillus amylophilus* GV6 using inexpensive carbon and nitrogen sources", *Journal of Applied Microbiology* 103 (2007) 372-380.
Demain et al., "Microbial Synthesis of Primary Metabolites: Current Advances and Future Prospects" from el-Mansi et al. eds. *Fermentation Microbiology and Biotechnology* $2^{nd}$ Ed.
Kious et al., "Lactobacillus and Lactic Acid Production", LeTourneau University, Applied Biological Sciences Branch, Alternative Fuels Division (2000) p. 5.
"Initiative to develop Alfalfa as a Feed Stock for bioenergy and bioproducts Production", National Alfalfa & Forage Alliance.
Werpy et al., "Top Value Added Chemicals From Biomass" (2004) p. 1.
Zhao et al., "Separation of solanesol in tobacco leaves extract by slow rotary counter-current chromatography using a novel non-aqueous two-phase solvent system", *Journal of Chromatography A*, 1151 (2007) 193-196.
Heenan et al., Growth Medium for Culturing Probiotic Bacteria for Applications in Vegetarian Food Products, *Lebensm.-Wiss. U.-technol.*, 35, 171-176 (2002).

* cited by examiner

COMPOSITION OF MATTER AND METHOD FOR STIMULATING THE GROWTH OF BENEFICIAL MICROORGANISMS

CROSS REFERENCE TO RELATED APPLICATIONS

This application is a National Stage of PCT/US2009/031995, filed Jan. 26, 2009, which claims priority from the provisional application Ser. No. 61/023,515, filed Jan. 25, 2008 and 61/106,426, filed Oct. 17, 2008, the entire contents of which are incorporated herein by reference.

GOVERNMENT INTERESTS

This invention was made with U.S. government support under USDA-CSREES Award No. 2006-33610-16829 and USDA-CSREES Award No. 2006-34467-17102. The government has certain rights in the invention.

PARTIES TO JOINT RESEARCH AGREEMENT

This invention arose out of a joint research agreement between the University of Maryland (College Park, Md.); NewAgriculture, Inc. (Port Tobacco, Md.), and Regional Policy Advisors (White Plains, Md.).

FIELD OF THE INVENTION

This invention relates to the use of leaf biomass to promote the growth of beneficial microorganisms in fermentation processes and to produce biobased chemicals and biofuels, prebiotics and other fermentation-based products.

BACKGROUND OF THE INVENTION

Many organic chemicals are manufactured using fermentation, including citric acid, acetic acid and lactic acid. Fermentation is also used to produce other products such as vitamins, amino acids, biofuels such as ethanol, enzymes or recombinant proteins. Demain, A. L and S. Sanchez, "Microbial Synthesis of Primary Metabolites: Current Advances and Future Prospects," in El-Mansi, E., C. Bryce, A. Demain and A. Allman (eds.), "Fermentation Microbiology and Biotechnology (2d ed). CRC Press, Boca Raton, Fla. (2007).

The cost of fermentation substrates is one of the largest costs associated with industrial fermentation. Vasileva-Tonkova, E., M. Nustorova and A. Gushterova, "New Protein Hydrolysates from Collagen Wastes Used as Peptone for Bacterial Growth. *Current Microbiology,* 54:54-57 (2007); Ezeji, T., N. Qureshi, H. Blaschek, "Butanol Production from Agricultural Residues: Impact of Degradation Products on *Clostridium beijerinckii* Growth and Butanol Fermentation." *Wiley Interscience,* (2007). Many organic chemicals which are now produced using petroleum-based raw materials could potentially be produced from renewable biobased raw materials through the use of industrial fermentation. In many cases, the high costs of existing fermentation substrates is a primary factor limiting the biobased production of these chemicals. Saha, B., "A low-cost medium for mannitol production by *Lactobacillus intermedius* NRRL B-3693. *Appl. Microbiol. Biotechnol.* 72:676-680 (2006). Among the many chemicals which could potentially be produced using fermentation are succinic acid, malic acid, glutamic acid, aspartic acid and 3-hydroxypropionic acid. Werpy, T. and G. Peterson (eds.), "Top Value Added Chemicals from Biomass." National Renewable Energy Laboratory and Pacific Northwest National Laboratory (August 2004).

The dramatic expansion in recent years of the biofuels and biobased products industries has created a new urgency to develop improved and less expensive fermentation substrates. In some cases, it is possible to use inexpensive sources of sugar such as glucose or sucrose and inexpensive sources of protein such as soy meal or corn steep liquor for fermentation processes. However, many organic chemicals cannot presently be effectively produced using these inexpensive products and require more complex and expensive substrates such as yeast extract, casein peptone or other peptones. However, it is also possible that supplementation of inexpensive sugar and protein sources with inexpensive new substrates might make it possible to produce organic chemicals which cannot now be produced through fermentation except with existing complex substrates.

Lactic acid is a chemical of particular interest. Long used in the food, chemical and pharmaceutical industries, lactic acid has attracted increasing attention in recent years due in part to its application in the manufacture of biodegradable polyacetate polymers, which are an alternative to non-biodegradable plastics.

Lactic acid can be industrially produced through fermentation, often using a lactic acid bacteria species such as the *Lactobacillus* sp. Kious, J., "*Lactobacillus* and Lactic Acid Production." National Renewable Energy Laboratory (2000). However, the costs of fermentation substrates are a major factor in production economics. Yeast extracts and peptones are important nitrogen sources for lactic acid production, with yeast extract typically accounting for approximately 38% of production medium costs. Altaf, M., M. Venkateshwar, M. Srijana and G. Reddy, "An economic approach for L-(+) lactic acid fermentation by *Lactobacillus amylophilus* GV6 using inexpensive carbon and nitrogen sources." *J. of Appl. Microbiol.* 103:372-380 (2007).

Another critical need in the industrial fermentation area relates to biofuels, i.e., fuels from biobased products. The bacterial species *Escherichia coli* (*E. coli*) is widely used in the production of ethanol, including cellulosic ethanol. *E. coli* can also be used to produce butanol and other ethanol alternatives. Thus substrates which can stimulate the growth of *E. coli* might have particular economic value.

Many current commercial microbial growth media are based on animal sources, such as milk or meat. This can pose risks of disease transmission, particularly if the fermentation product is intended for human consumption. In addition, use of animal-derived media is inappropriate if the fermentation products intended for vegetarians. Therefore, there is an interest in new plant-based growth media to replace existing milk or meat-based products.

In addition to industrial fermentations, fermentation substrates can also be used to as "prebiotics", i.e., substances used to stimulate the growth of "probiotic" microorganisms. A probiotic is a live microbial food supplement that beneficially affects a host animal by improving its intestinal microbial balance, particularly the environment of the gastrointestinal tract. Probiotics are consumed either in food products or as dietary supplements. Postulated health advantages associated with probiotic intake are the 1) alleviation of symptoms of lactose malabsorption; 2) increase in natural resistance to infectious diseases of the intestinal tract; 3) suppression of cancer; 4) reduction in serum cholesterol concentrations; 5) improved digestion; and 6) stimulation of gastrointestinal immunity.

Prebiotics are used to stimulate the growth of probiotics. A prebiotic is a non-digestible food ingredient that beneficially affects the host by selectively stimulating the growth, activity, or both of one or a limited number of bacterial species already resident in the colon.

Yeh et al. found that a leaf hydrolysate prepared using the Chinese wolfberry, a medicinal herb widely used in Asia as a tea, somewhat stimulated the growth of the probiotic bacterial species *Pediococcus acidilactici*, compared to a control containing the bacterial growth medium MRS (de Man, Ragosa and Sharpe). Yeh, Y-C et al., "Effects of Chinese wolfberry (*Lycium chinense* P. Mill.) leaf hydrolysates on the growth of *Pediococcus acidilactici*." *Bioresource Technology* 99: 1383-1393 (2008). The authors reported an approximately 2.5-fold increase in growth using a 20% treatment of the hydrolysate in an MRS medium compared to an MRS control. The authors reported *P. acidilactici* concentrations of about $5.5 \times 10^9$ CFU/ml after 24 hours. Based on this result, the authors suggested that wolfberry leaf hydrolysate may have potential for promoting the growth of probiotic bacteria. The authors did not evaluate or discuss the potential of wolfberry leaf hydrolysate to promote the growth of organic acids, nor did they raise the possibility of its suitability as a substrate in industrial fermentations.

Martin et al. found that hydrolysates prepared from tobacco stalks showed potential as raw material for conversion to cellulosic ethanol by fermentation with baker's yeast. Martin, C., et al., "Preparation of hydrolysates from tobacco stalks and ethanolic fermentation by *Saccharomyces cerevisiae*," *World J. Microbiol & Biotechnol*. 18: 857-862 (2002). These researchers, however, only discussed conversion of the stalk matter, and did not discuss hydrolysis or other uses of the leaf. Furthermore, their research was limited to the suitability of tobacco stalks as a raw material for conversion to ethanol. They did not discuss the potential of tobacco stalks to serve as a substrate in the production of industrial chemicals.

Pandolfino reported that it was possible to produce ethanol from tobacco plants using a recombinant low-nicotine tobacco variety. U.S. Patent Application 20020197688 (Dec. 26, 2002). Pandolfino explained that ethanol could be produced by fermenting the plant in a fermentation vessel for a time sufficient to produce ethanol therefrom; and then collecting the ethanol from the fermentation vessel. Unlike Pandolfino, the claimed invention does not require a recombinant tobacco variety. Furthermore, the claimed invention does not relate to a method for producing ethanol but rather to produce a microbial growth promoter.

Levie et al. disclosed a method for producing a hydrolysate from lignocellulosic materials which involved fiberizing the materials and then separating them into two different portions. U.S. Patent Application 20080227161 (Sep. 18, 2008). The first portion would then be treated to deactivate lignin, and then the two portions would then be recombined prior to hydrolysis of the lignocellulosic materials. The resulting hydrolysate could then be fermented into ethanol. Levie's method required separation of the fiberized materials into two portions, with at least the first portion containing lignin, and then treating the first portion prior to recombination of the two portions and then hydrolyzing the combined materials with enzymes. Their objective was to use the hydrolysate to produce ethanol, as opposed to using it to stimulate microbial growth. In contrast to Levie, the claimed method does not relate to a microbial growth promoter and it does not require separation of the biomass into multiple portions.

Fichtali et al. taught a method for developing a stable composition by emulsifying a biomass hydrolysate which contained a desired nutrient. U.S. Patent Application 20060286205 (Dec. 21, 2006). The resulting emulsion product could be incorporated, into, or used as, nutritional products, cosmetic products or pharmaceutical products. The invention particularly related to stable compositions comprising at least one long chain polyunsaturated fatty acid. In contrast to Fichtali, the claimed method does not involve emulsification of the biomass hydrolysate. Also unlike Fichtali, the claim invention relates to a microbial growth promoter which is not one of the products produced through Fichtali's method.

There remains a need in the art for low cost materials that can be used to grow microorganisms. This need and others are met by the present invention.

SUMMARY OF THE INVENTION

The present invention provides methods for preparing a novel composition of matter known as leaf biomass hydrolysate (LBH). LBH may be thought of, roughly, as a nutrient-rich composition derived by extracting nutrients from plant leaf matter. LBH prepared according to the methods of the invention may be used for any suitable purpose, for example, in promoting the growth of microorganisms. For example, utilizing varying concentrations of LBH, the inventors were able to obtain more than an eight-fold increase in the growth of a probiotic bacteria species compared with standard microbial growth media used to promote probiotic bacterial growth. This result indicates that LBH can be useful as a prebiotic. Microorganisms grown using LBH prepared according to the present invention may be used for other purposes, for example, in the fermentation-based production of chemicals, biofuels, vitamins, vaccines, enzymes and recombinant proteins.

The invention described herein contemplates the use of many species of plants as a suitable input for the production of LBH. Examples of suitable plants include, but are not limited to, leafy plants such as *Nicotiana* species, alfalfa, or spinach, amongst others which one skilled in the art will recognize.

Methods of the invention may typically involve, first, disrupting plant leaves using any suitable technique, for example, pressing, milling, grinding etc. Following this disruption, the practitioner may then extract one or more desirable leaf components from the disrupted leaf matter. For example, the practitioner may extract some or all of the soluble leaf proteins using any suitable leaf protein extraction method in order to use the leaf protein as a separate and unrelated byproduct. A non-limiting list of other desirable leaf components which the practitioner may wish to extract include plant secondary metabolites, recombinant proteins or enzymes. Such desirable leaf components may be extracted using suitable methods known to practitioners. For purposes of the claimed invention, the term "desirable leaf components" refers to one or more of leaf proteins, recombinant proteins, secondary metabolites, enzymes or other leaf materials which are removed or extracted by the practitioner in the course of preparing LBH, typically for use in separate products or processes. Following any removal of desirable leaf components that may be performed, the leaf matter for use in the present invention may optionally be sterilized. Following this optional sterilization, the disrupted leaves may then incubated in a liquid. After incubating the leaf-containing liquid may be further processed, for example, by filtration. Optionally, the LBH containing liquid may be condensed, dried, or dehydrated into a condensed liquid or powder.

DETAILED DESCRIPTION OF THE INVENTION

Figure 1:
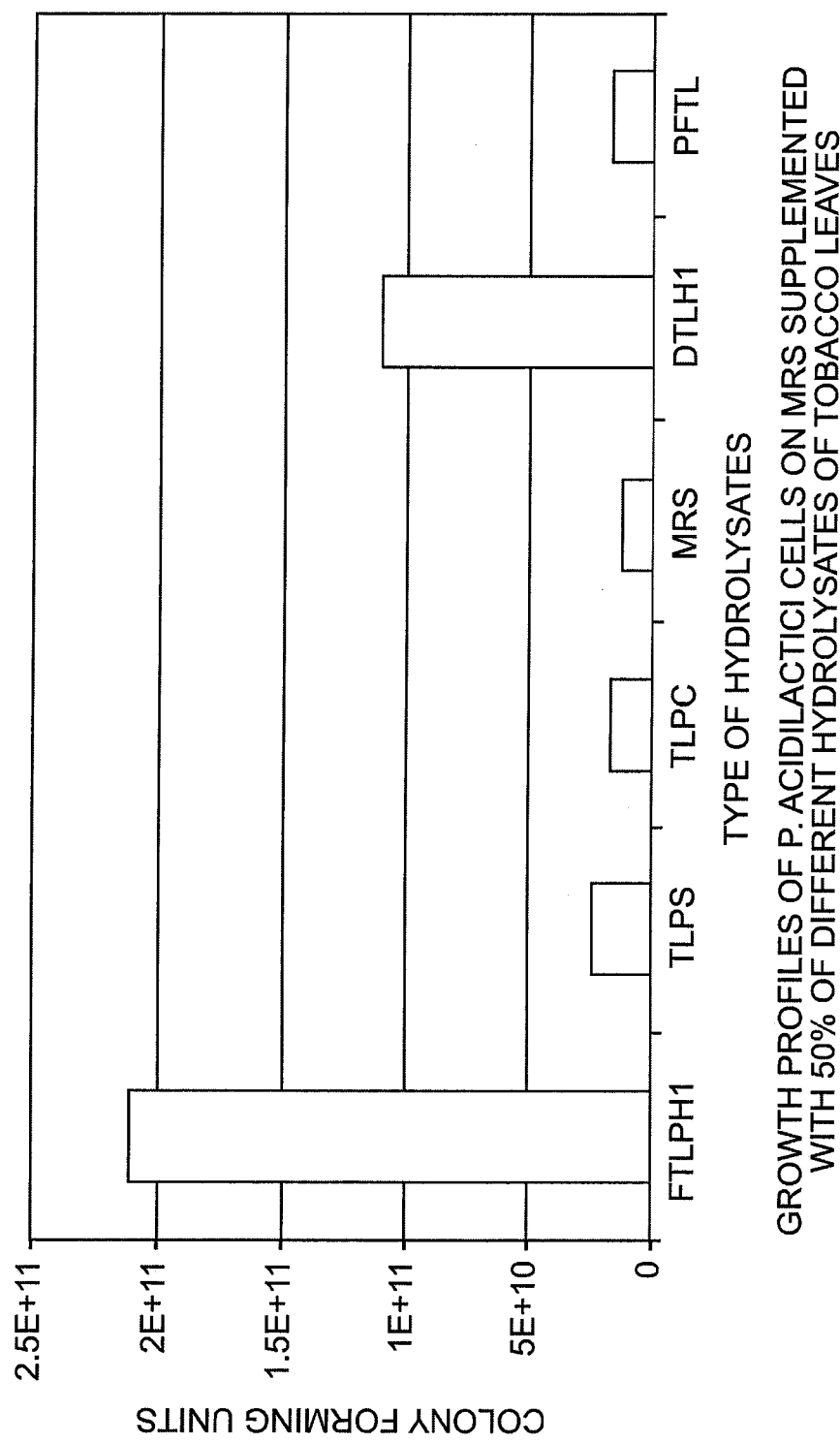
FIG. 1: Growth Profiles of *P. Acidilactici* cells on MRS supplemented with 50% mixtures of different hydrolysates of tobacco leaves and tobacco leaf protein. FTLPH1=fresh sterilized and squeezed tobacco leaf hydrolysate added at a 1:1 volumetric with MRS agar. TLPS=Tobacco leaf solid protein at a 1:1 volumetric with MRS agar. TPLC=Tobacco leaf crystal protein at a 1:1 volumetric with MRS agar. MRS=MRS agar (control). DTLH1=Dried tobacco leaf hydrolysate obtained following soluble protein extraction at a 1:1 volumetric with MRS agar. PFTL=Powdered fresh tobacco leaf obtained following protein extraction from the pilot plant at a 1:1 volumetric with MRS agar.

The principles, preferred embodiments and modes of operation of the present invention will be described hereunder. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the examples, descriptions, and best mode of carrying out the invention given below should be considered exemplary in nature and not as limiting to the scope and spirit of the invention as set forth in the claims.

The inventors have unexpectedly found that use of hydrolyzed biomass from plant leaves (e.g., tobacco leaves) dramatically stimulates the growth of beneficial microorganisms which are used in fermentation processes. Our data indicates that a "tea" prepared using the hydrolyzed leaf biomass from tobacco ("TLBH", or "tobacco leaf biomass hydrolysate") dramatically stimulated the growth of beneficial microorganisms. In addition, use of the hydrolyzed tobacco leaf biomass can stimulate the rapid growth of organic acids and *E. coli* bacteria. We found that application of the same "tea-making" method for preparing leaf biomass hydrolysates using other plant species also stimulates the growth of beneficial microorganisms. The inventors also unexpectedly found that leaf biomass hydrolysates continue to demonstrate a dramatic stimulatory effect on growth of beneficial microorganisms even when desirable leaf components (e.g., soluble leaf proteins, etc.) are removed while preparing the leaf biomass hydrolysates. The costs of producing leaf biomass hydrolysates are also substantially lower than the costs of producing most complex fermentation substrates such as peptones or yeast extracts. Therefore, leaf biomass hydrolysates are useful as a substrate to promote the growth of beneficial microorganisms and in the production of biobased chemicals or biofuels.

LBH is a novel composition of matter which results from (1) optionally disrupting freshly harvested or stored plant leaves; (2) optionally extracting desirable leaf components from the leaf biomass, such as soluble leaf proteins, enzymes, recombinant proteins, or secondary metabolites; (3) optionally sterilizing the leaf matter; (4) incubating the leaf matter in a suitable solvent (e.g., sterilized or distilled water) in order to extract the soluble leaf constituents and produce a liquid containing the soluble constituents; (5) optionally filtering the liquid to remove solid materials; and (6) optionally, drying down the filtered liquid to produce a powder.

Preparation of LBH

LBH may be produced using plant leaves from a variety of plant species, such as tobacco, spinach, or alfalfa, amongst others which one skilled in the art will recognize. It is particularly preferred to harvest plant leaves during their green vegetative stage and then process them as described in this application promptly following harvest. Prompt processing minimizes breakdown of the leaf sugars and proteins. As an alternative, the leaves can be refrigerated or frozen until ready for processing. Cooling the leaves will slow or prevent breakdown of sugars and proteins.

Following harvest or storage (as applicable), typically the leaves may be initially disrupted, crushed, pressed or chopped into small pieces. Any commonly used process for disrupting or chopping the leaf is acceptable, including chopping, milling, grinding or crushing the leaves, pulping, maceration procedures, mechanical pressure, rollers or homogenizing, among other such procedures which one skilled in the art will recognize. In a preferred embodiment, the disrupted leaves are also pressed, squeezed or rolled. This pressing, squeezing or rolling removes a substantial portion of the water from the leaves, along with water-soluble proteins contained in that water.

Following leaf disruption, desirable leaf components of interest to the practitioner may be extracted from the disrupted leaf. Such desirable leaf components may include, without limitation, soluble leaf proteins, enzymes, recombinant proteins or secondary metabolites. For example, in the cases of tobacco, alfalfa or spinach leaf biomass, the practitioner may wish to extract soluble leaf proteins from the disrupted tobacco leaf. Johal, U.S. Pat. No. 4,334,024 (June 1982). Some species, such as tobacco and alfalfa, have been utilized as host species for the production of recombinant proteins by academic researchers and by companies such as Kentucky Bioprocessing, LLC (Owensboro, Ky.), and Medicago, Inc. (Quebec City, Quebec), and the practitioner may wish to extract such recombinant proteins. Examples of secondary metabolites of tobacco which may be desirable leaf components for a practitioner include nicotine, which is an insecticide, and solanesol, which is used in the production of nutraceuticals. Zhao, Y. and Q. Du, "Separation of solanesol in tobacco leaves extract by slow rotary counter-current chromatography using a novel non-aqueous two-phase solvent system." *J. of Chromatography A*. 1151: 193-196 (2007). Examples of secondary metabolites in alfalfa which may be desirable leaf components include flavonoid antioxidants and phytoestrogens, which could be potential nutraceuticals. National Alfalfa and Forage Alliance, "Initiative to Develop Alfalfa as a Feedstock for Bioenergy and Bioproducts Production."

In a preferred embodiment, the leaves are sterilized in order to prevent the growth of microbial contaminants which may be present on the leaves. A preferred embodiment is to sterilize the leaves by drying them to a water activity level of approximately 0.85 or below. The leaves can be dried using any suitable drying technology such as oven drying or tunnel drying. As an alternative embodiment, the leaves can be sterilized with any suitable sterilizing agent such as ethanol, bleach, ozone, UV light, radiation, amongst other methods which one skilled in the art may recognize.

As an alternative embodiment, it is possible to vary the sequence of the above-mentioned disruption, extraction and sterilization steps. For example, the practitioner may elect to first sterilize the leaves prior to disrupting them or prior to extracting desirable leaf components.

It is possible at this point in the LBH preparation process for the practitioner to package or commercially provide sterilized and/or disrupted leaves for distribution to users or customers. The leaves may be packaged in filter paper or in any other container which permits soluble leaf nutrients to be extracted and filtered out into water or other solvent. Alternatively, the leaves may be ground into a powder prior to distribution. Or alternatively, the sterilized and disrupted leaves may be distributed to users in their leaf form. In the event that the practitioner elects to distribute the leaves to users or customers as described in this paragraph, then the user or customer would perform the remainder of the LBH preparation steps described in the succeeding paragraphs.

Following the optional leaf disruption and sterilization and the removal of desirable leaf components, the leaves may then be incubated in a solvent suitable for extracting the soluble leaf components. Such solvents may include water, ethanol, acetone, etc, which one skilled in the art will recognize. The solvent (e.g., water) may be heated to between 60° C. and 90° C. in order to solubilize the constituents of the leaves. In a preferred embodiment, the leaves are heated at a temperature between 75° C. and 85° C. in water. In one preferred embodiment, the water used will be boiled tap water to minimize the risk of microbial contamination. In an especially preferred embodiment, the water used should be distilled water to minimize risks of microbial contamination or impurities caused by minerals or heavy metals. Leaves should be heated in solvent (e.g., water) for at least 15 minutes, but may be heated for as long as a week or more. In a preferred embodiment, leaves should be heated for between 30 minutes and 24 hours. In a particularly preferred embodiment, leaves should be heated for between 30 minutes and eight (8) hours. In an especially preferred embodiment, leaves should be heated for between 30 minutes and two (2) hours. This incubation treatment produces a liquid containing soluble compounds. If the incubation treatment was performed in water, the liquid will contain water-soluble compounds. In a preferred embodiment, the ratio of leaves to hot water should be about 10 grams of leaves to between 100 and 300 ml. of water. Use of higher leaf concentrations results in a cloudiness in the water and appears to inhibit the effectiveness of the product in stimulating microbial growth. Use of excess quantities of water (or other solvent) is inefficient and costly.

The hydrolysate may then be filtered using any suitable filtration equipment to remove solid material. Following filtration, the liquid containing the soluble compounds may be dried down to a concentrated liquid or powder. Exemplary drying techniques include spray drying to a powder product, or evaporation to produce a liquid concentrate, amongst many other drying/dehydration techniques which one skilled in the art will recognize.

The end product is a novel composition of matter, specifically a powder (if drying is performed) or liquid (if drying is not performed) containing the soluble constituents of the leaf biomass (excluding any desirable leaf components which were removed). In a preferred embodiment in which leaf disruption and sterilization were performed and distilled water was the incubation liquid, the end product is a liquid or powder consisting of the sterilized water-soluble constituents of the disrupted leaf biomass.

For purpose of this application, the terms "leaf biomass hydrolysate" or "LBH" refers to a liquid or solid product which results from the process described in this Detailed Description of the Invention. The terms "tobacco leaf biomass hydrolysate" or "TLBH" refer to leaf biomass hydrolysate obtained from tobacco leaves.

Applications of LBH

Figure 5:
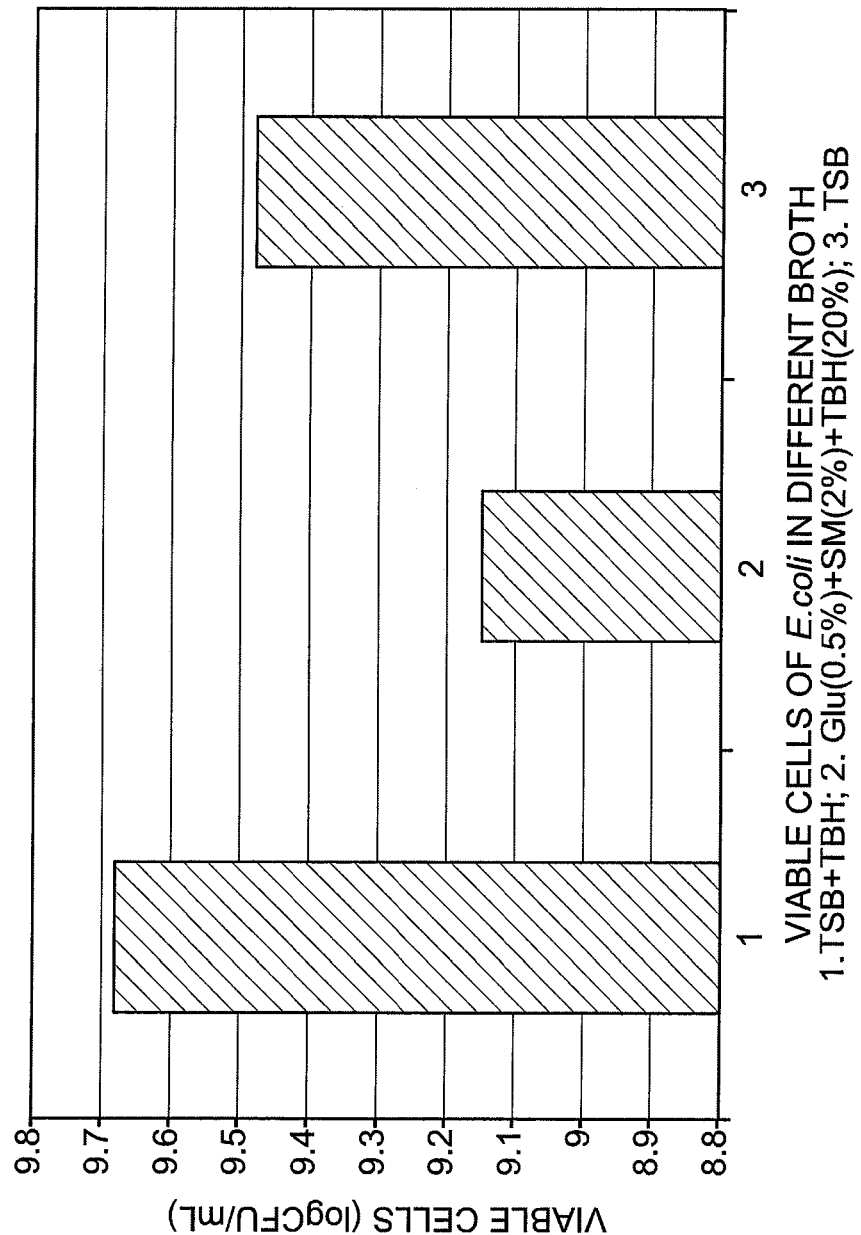
FIG. 5: Graph comparing growth of *E. coli* bacteria cells in Tryptic Soy Broth (TSB) and TSB+20% TLBH. TSB=Tryptic soy broth; TBH=Tobacco leaf biomass hydrolysate; Glu=Glucose; SM=Soy Meal. 1. TSB+TBH; 2. Glu (0.5%)+SM(2%)+TBH(20%); 3. TSB
Figure 6:
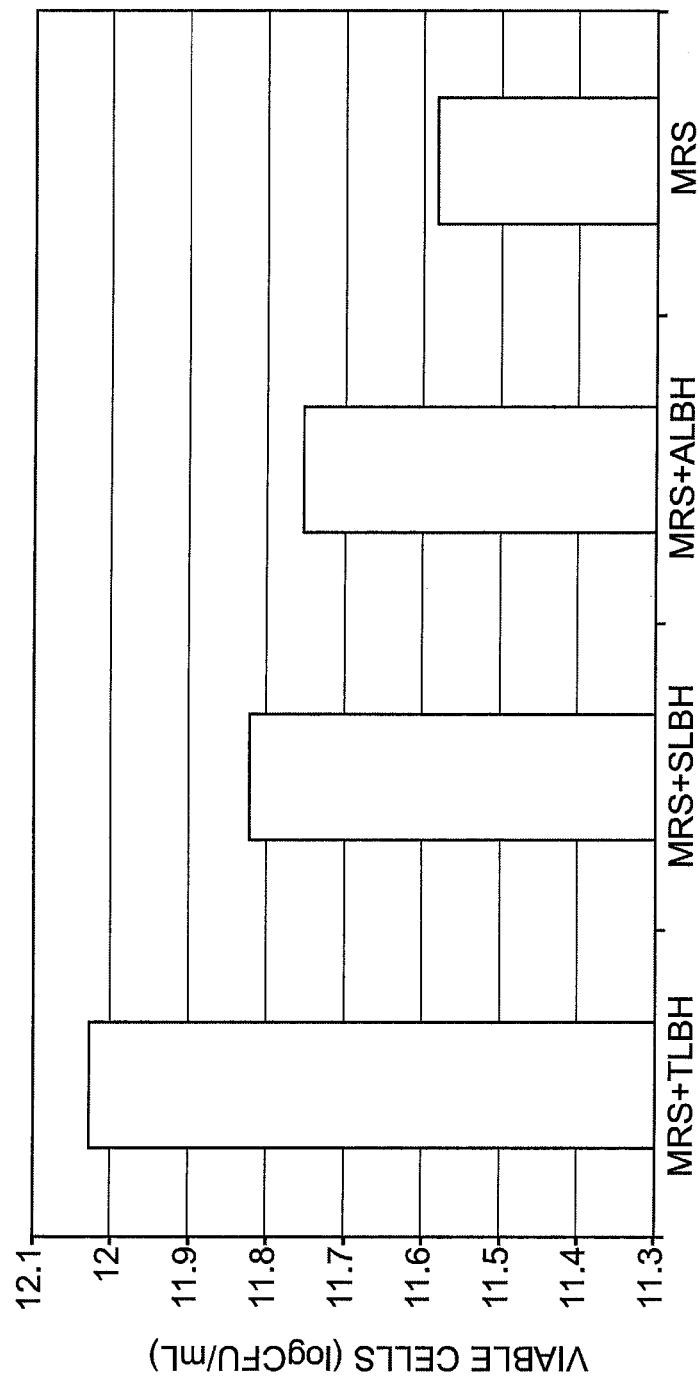
FIG. 6: Graph comparing growth of *P. acidilactici* using various growth media. The graph compares growth after twelve hours using standard MRS media with MRS media supplemented with tobacco leaf biomass hydrolysate (TLBH), spinach biomass hydrolysate (SLBH), and with biomass hydrolysate (ALBH).

LBH can stimulate microbial growth and is useful in the fermentation-based production of organic chemicals, biofuels, probiotics vitamins, vaccines, recombinant proteins, enzymes or other products. LBH may be utilized as a sole feedstock, or may be used in a mixture with other microbial growth media such as MRS agar or TSB (tryptic soy broth) to enhance microbial growth (FIGS. 1, 2, 3 and 5 and 6) or to produce organic acids (FIG. 4), biofuels or other fermentation-based products. There is a broad range of commercially available microbial growth media. For purposes of this application, the terms "commercially available prokaryotic growth media" and "commercially available eukaryotic growth media" refer, respectively, to prokaryotic and eukaryotic growth media which are available from commercial suppliers, examples of which include Sigma-Aldrich, Invitrogen, BD, DIFCO and Fisher-Scientific. In addition, LBH may be used as a supplement to inexpensive sources of protein, such as soy meal, corn steep liquor or the like, and carbohydrates, such as glucose, sucrose, starch, molasses or the like, either with or without commercial growth media, to produce organic chemicals and other products through fermentation which would otherwise have generally required complex substrates for fermentation-based production (FIG. 6).

Based on the information described above and the examples provided below, the uses and applications of LBH include the following non-limiting list.

Figure 4:
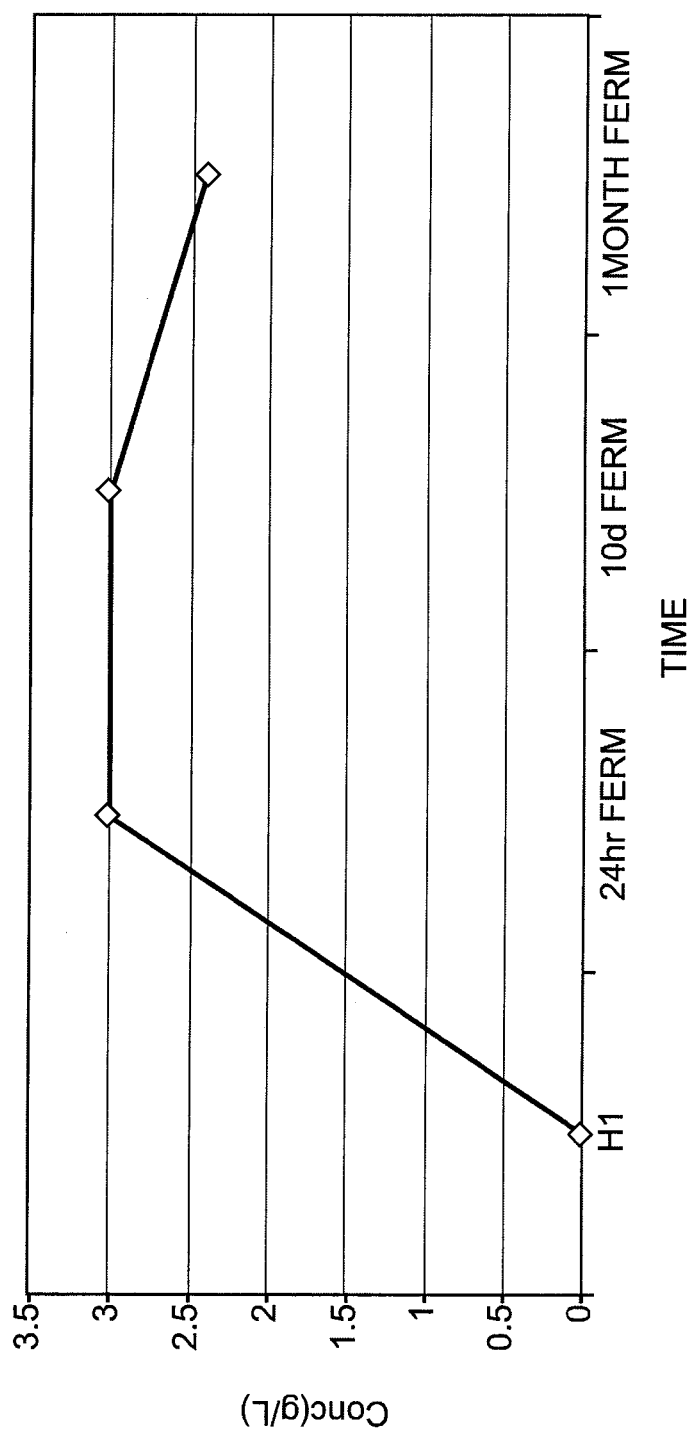
FIG. 4: is a graph showing the lactic acid production resulting from fermentation with TLBH. Lactic acid concentration was determined by HPLC analysis.

1. Use as a substrate in industrial fermentations in the production of organic acids and other organic chemicals (FIG. 4). A partial list of the potential chemicals which might be produced using LBH as either the sole substrate or as a component in a microbial growth medium or a solution or mixture includes (but is not limited to) the following: lactic acid, propionic acid, acetic acid, succinic acid, malic acid, glutamic acid, aspartic acid and 3-hydroxypropionic acid, as well as their analogs, homologs, or derivatives. The fermentation conditions to produce lactic acid or lactate (salts of lactic acid) are well known. (Otto, R., U.S. Pat. No. 7,083, 955 (Aug. 1, 2006) which is specifically incorporated herein for its disclosure of fermentation conditions). The temperature may range from 0° to 80° C., although an optimal temperature for *Lactobacillus* fermentation of lactic acid is 37° C. (Otto, 2006; Kious, 2000). The pH may range from 3 to 8, although a lower pH reduces the risk of contamination with other microorganisms (Otto, 2006). Other organic chemicals include antibiotics, for example, those that may be produced by fermentation of *Streptomyces* sp. In fact, any organic chemical which is potentially producible through fermentation could potentially utilize LBH as a substrate.

2. Production of biofuels. A substantial portion of biofuel production, including traditional ethanol production, cellulosic ethanol, butanol, and other possible biofuels, utilizes *E. coli*. The inventors found that a solution containing 20% LBH prepared from hydrolyzed tobacco leaf biomass+80% tryptic soy broth (TSB, a commercial growth medium used for *E. coli*) promoted *E. coli* growth more effectively than a control containing 100% TSB (FIG. 5). In fact, the inventors were able to establish colonies of *E. coli* using TLBH on an autoclaved agar as the substrate (Example 5). These results indicate that LBH (for example, TLBH) is a suitable substrate for *E. coli* in the production of biofuels.

3. Supplement to Low-Cost Substrates in Fermentation Processes. LBH can also be used as a supplement to inexpensive protein and carbohydrate sources to make it possible to produce many products which now require complex substrates for fermentation-based production. While inexpensive fermentation sources of carbohydrates such as glucose and sucrose and inexpensive sources of protein such as soy meal or corn steep liquor exist, they are insufficient for the fermentation-based production of many products. LBH could be added to inexpensive or simple substrates to produce many products which now require complex or expensive substrates for fermentation-based production. Similarly, addition of LBH could reduce the amount of expensive or complex substrates which are needed to produce various products through fermentation. Use of LBH in microbial growth media could make possible and feasible the production of many organic chemicals and other products which cannot now be produced (or cannot economically be produced) through fermentation processes. (See treatment 2 in FIG. 6, demonstrating significant *E. coli* colony formation using a substrate containing TLBH from tobacco combined with low-cost protein and carbohydrate sources and only low levels of commercial growth media).

4. Use as a prebiotic to stimulate growth of probiotic bacteria (FIGS. 1, 2, 3, and 5).

5. Use in the fermentation-based production of vitamins. Lactic acid bacteria are used in the fermentation-based production of vitamins, and *E. coli* can also produce vitamins including vitamin K-2. The inventors have demonstrated that LBH stimulates the growth of lactic acid bacteria species such as *Pediococcus* species and *E. coli* (FIGS. 1, 2, 3, 5 and 6). This is evidence that LBH can be used in the fermentation-based production of vitamins.

6. LBH can also be used for any fermentation-based processes which utilize *E. coli* (FIG. 5). A partial list of these processes and uses include production of recombinant proteins, vaccine production, bioremediation, and production of immobilized enzymes and organic chemicals.

EXAMPLES

The inventors have demonstrated the effects of LBH in promoting microbial growth using tobacco leaf biomass. The invention is further described in the non-limiting examples described below.

Example 1

Comparison of different tobacco leaf biomass fractions with a standard microbial growth promoter in promoting bacterial growth The purpose of this experiment was to assess the effect of different tobacco leaf biomass and protein fractions in promoting the growth of a beneficial probiotic bacterial species. The different fractions were compared with a standard commercial growth medium for promoting probiotic acid bacterial growth.

The analyses utilized the probiotic bacterial species, *Pediococcus acidilactici*, which is contained in several commercial probiotic feeds and which has been recovered from a wide range of animal species. The analyses utilized materials obtained from plants of the low-alkaloid tobacco variety MD 609LA. All samples involved materials which had been harvested from tobacco plants in their green, vegetative state.

The test compared five treatments:

Treatment 1: ("FTLPH1"): a hydrolysate containing fresh, sterilized tobacco leaves prepared without any recovery of soluble leaf proteins, prepared at a 1:1 volumetric with MRS agar;

Treatment 2 ("TLPS"): solid soluble protein obtained from tobacco leaves at a 1:1 volumetric with MRS (Man, Rogosa and Sharpe) agar;

Treatment 3: ("TPLC"): Tobacco leaf crystal protein at a 1:1 volumetric with MRS agar;

Treatment 4: ("DTLH1"): Dried tobacco leaf hydrolysate obtained following soluble leaf protein extraction at a 1:1 volumetric with MRS agar. This treatment is what we refer to as tobacco leaf biomass hydrolysate or "TLBH."

Treatment 5: ("PFTL"): Powdered fresh tobacco leaf obtained following soluble leaf protein extraction from the pilot plant at a 1:1 volumetric with MRS agar.

Figure 7:
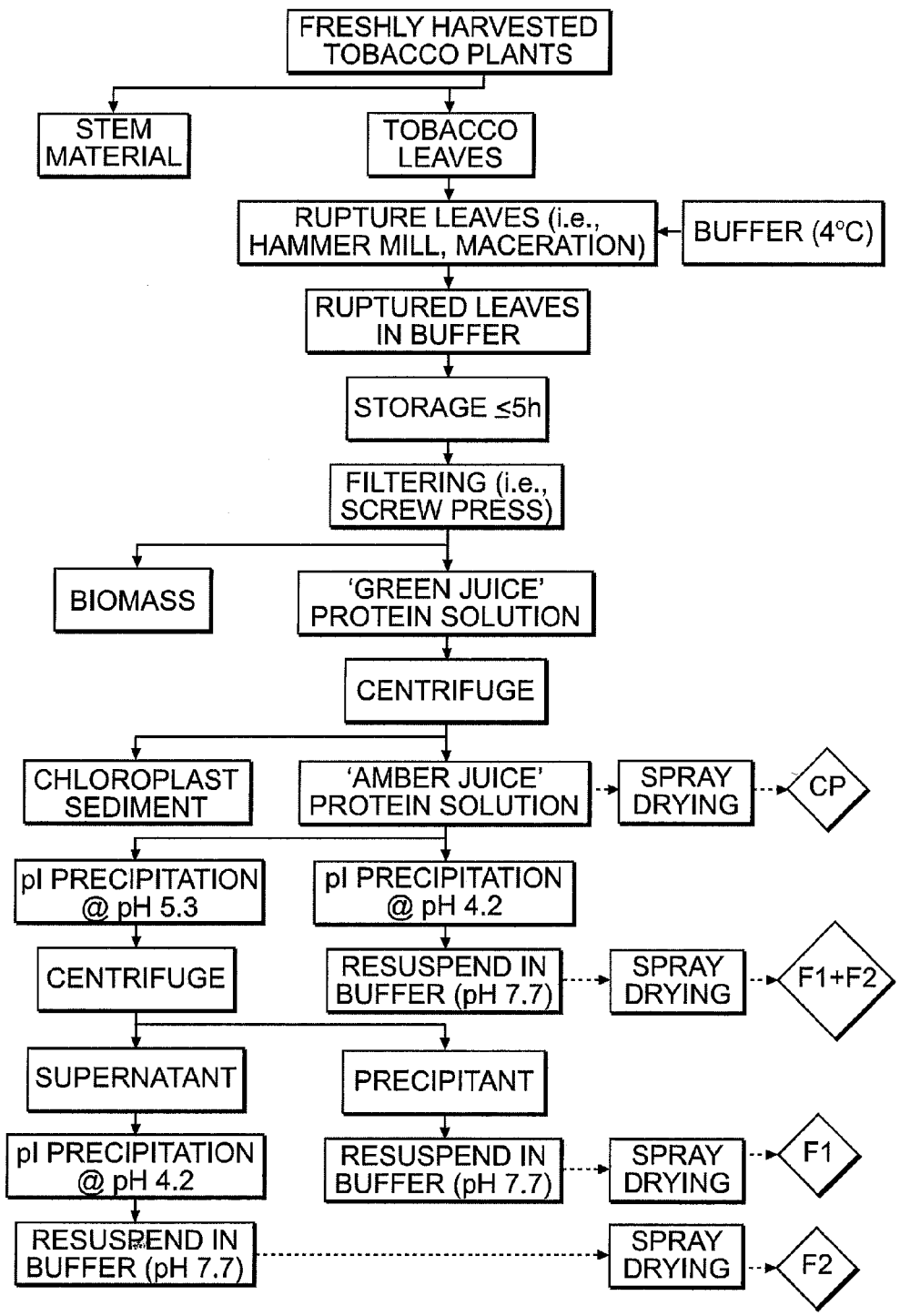
FIG. 7: Leaf Protein Recovery Process in Tobacco.

A flow-chart showing the leaf protein extraction process utilized in preparing several of the above-mentioned treatments available at FIG. 7.

In Treatment 1 (FTLPH1), fresh green tobacco leaves were refrigerated promptly after harvest. The unprocessed refrigerated leaves were then sterilized using alcohol at 70° F., and then bleach at 0.5%, and then washed three times using distilled water. The leaves were subsequently dried on paper. The dried leaves were mechanically squeezed to improve the extractability of the nutrients. There was no extraction of leaf proteins in this treatment.

Treatment 2 (TLPS) was a crude protein powder prepared from tobacco leaves. It was prepared using the following steps: (a) Freshly harvested leaves were ruptured using a hammermill in the presence of a buffer solution containing 0.067M $Na_2HPO_4$—$KH_2PO_4$ at pH 7.77. (b) The ruptured leaves were then stored in refrigeration for approximately five hours, after which they were filtered using a screw press. This filtering process resulted in two separate fractions—the green juice containing soluble leaf proteins, and the biomass. (c) For treatment 2, we utilized the green juice fraction. We centrifuged the green juice to remove the plant chloroplast material, resulting in an "amber juice" containing the soluble leaf proteins. (d) We then spray dried this amber juice, resulting in a crude protein powder (referred to as "CP" in FIG. 7). This crude protein became our Treatment 2.

Treatment 3 (TPLC) contained crystallized tobacco leaf proteins. We followed the same procedures as in preparing treatment 2 above, except that we did not spray dry the amber juice. Rather, we prepared an isoelectric point precipitation on the amber juice at pH 5.3 to separate the crystallizing fraction-1 proteins (also known as "rubisco") from the other plant leaf proteins (fraction-2 proteins). We then centrifuged the solution, and kept the precipitant. We then added ammonium sulfate to the precipitant. We permitted this solution to precipitate and then collected the precipitated material. We then resuspended the precipitated material in the buffer solution 0.067M $Na_2HPO_4$—$KH_2PO_4$ at pH 7.77 and allowed the product to remain in resuspension, which resulted in the crystallization of rubisco. We collected this crystallized rubisco, and this rubisco became our treatment 3.

Treatment 4 (DTLH1). This treatment represents what is referred to herein as tobacco leaf biomass hydrolysate or "TLBH." Steps (a) and (b) were identical to Treatment 2 above. However, for Treatment 4, we utilized the biomass fraction and not the green juice fraction. (The biomass fraction is designated as "Biomass" in the flow chart in FIG. 7). The biomass was oven-dried at 60° C. for 12 hours for sterilization, and then sealed in air-tight plastic bags.

Treatment 5 (PFTL). Steps (a) and (b) were identical to Treatment 4 above. And just as in Treatment 4, we selected the biomass fraction and not the green juice fraction. However, we ground the biomass into a powder rather than oven-drying it.

Samples from all four treatments were stored at 4° C. prior to use. Each of these treatments was then prepared in a 1:1 solution with MRS agar (i.e., each sample contained 50% sample+50% MRS agar on a v/v basis). MRS agar is a standard growth medium for probiotic bacteria. The analyses also included a control containing only MRS agar.

For each of the three leaf samples a "tea" was prepared (Treatments 1, 4 and 5). Five (5) grams of leaves were placed into a 250 ml beaker containing 150 ml of distilled water, and then heated the beaker in a water bath at 75° C. for 1 hour. The sample material was then filtered through a Whatman No. 41 paper filter and collected into a centrifuge tube. The treatment was then prepared by using a 1:1 volumetric ratio with the sample and MRS agar.

For each of the two protein treatments (Treatments 2 and 3), 60 ml of distilled water was added to the sample, which was filtered through paper filter, and used at a 1:1 volumetric ratio with MRS agar.

Plates containing $P.$ $acidilactici$ were incubated at 37° C. for 72 hours. A count of colony forming units (CFU's) was performed at 48 hours. The results of the 48-hour count are presented in FIG. 1.

The inventors found that TLBH (treatment 4) produced a dramatic and unexpected stimulatory effect upon microbial growth. TLBH produced more than an eight-fold increase in bacterial growth compared to the MRS control. (FIG. 1). Specifically, the inventors found that the growth of $P.$ $acidilactici$ on a 1:1 mixture of TLBH and MRS agar yielded a cell concentration of $1.1*10^{11}$ CFU/ml. This cell concentration is more than 20 times greater than that reported by Yeh et al. (above) using a 20:80 Wolfberry:MRS mixture. This result indicated that the 1:1 supplement of TLBH dramatically increased bacterial growth compared with the MRS control.

In fact, one other treatment performed somewhat better than TLBH. Treatment 1, which involved substantially the same preparation as TLBH except that no leaf protein was removed, actually yielded approximately double the growth of $P.$ $acidilactici$ than the TLBH treatment, producing a cell concentration of $2.3 \times 10^{11}$ CFU/ml. This indicates that removal of the water-soluble leaf protein does reduce bacterial growth somewhat. However, the advantage of removing the leaf protein prior to preparation of TLBH is that it permits recovery of a leaf protein co-product while still dramatically stimulating bacterial growth.

All of the other treatments produced less growth than treatment 2 by nearly a factor of 10. Treatment 2 (the tobacco protein powder) produced $2.3 \times 10^{10}$ CFU/ml. The tobacco protein crystal produced $1.6 \times 10^{10}$ CFU/ml. The fresh tobacco obtained (without drying) following soluble protein extraction produced $1.6 \times 10^{10}$ CFU/ml. The growth of $P.$ $acidilactici$ on MRS agar (control) showed the least cell concentration ($1.3 \times 10^{10}$ CFU/ml).

In conclusion a 1:1 TLBH-MRS mixture (prepared using TLBH from dried leaves following leaf protein extraction) yielded more than an 8-fold increase in cell concentration of the prebiotic bacteria $P.$ $acidilactici$ compared with the standard prebiotic growth medium MRS alone. An ideal growth medium should be able to promote bacterial growth up to $10^9$ CFU's. Heenan, C., M. Adams, R. Hosken and G. Fleet, "Growth Medium for Culturing Probiotic Bacteria for Applications in Vegetarian Food Products." $Lebenssm.$-$Wiss.$ $U$-$Technol$ 35:171-176 (2002). TLBH, when provided in a 1:1 mixture with MRS, exceeded this threshold by over 100 times.

Without wishing to be bound by theory, the inventors believe that the very strong growth of TLBH following extraction of soluble leaf proteins is due in part to several factors. First, existing leaf protein technology does not necessarily extract all soluble leaf protein, and the remaining leaf protein may be sufficient for fermentation processes. Second, in addition to soluble leaf protein, the plant cell walls contain bound proteins which are not removed from the pressing or extraction process, and these bound proteins may be available in fermentation processes. In addition, as discussed below, TLBH contains both high levels of glucose and a wide range of trace elements and therefore appears to be an excellent substrate.

Example 2

Comparison of TLBH and MRS

The inventors conducted a follow-up test involving only TLBH and MRS. In this experiment, the inventors followed the leaf protein recovery process as described in Treatment 4 of Example 1 above, and as above, they selected the biomass fraction for this study. They then oven-dried the biomass at 55° C. for 40 hours. Ten (10) grams of dried leaves were then placed in a 250 ml beaker containing 200 ml of distilled water and heated in a water bath at 85° C. for 1 hr. The hydrolysate was filtered through a Whatman No 1 filter paper and then cooled to room temperature prior to use.

$P.$ $acidilactici$ cells were inoculated into a control containing MRS broth and into a treatment in which 10% of the MRS had been replaced by TLBH on a v/v basis (i.e., a 10:90 TLBH:MRS treatment). Cells of both treatments were incubated for 24 hours, at 37° C., and then a cell count was taken at 24 hours.

Figure 2:
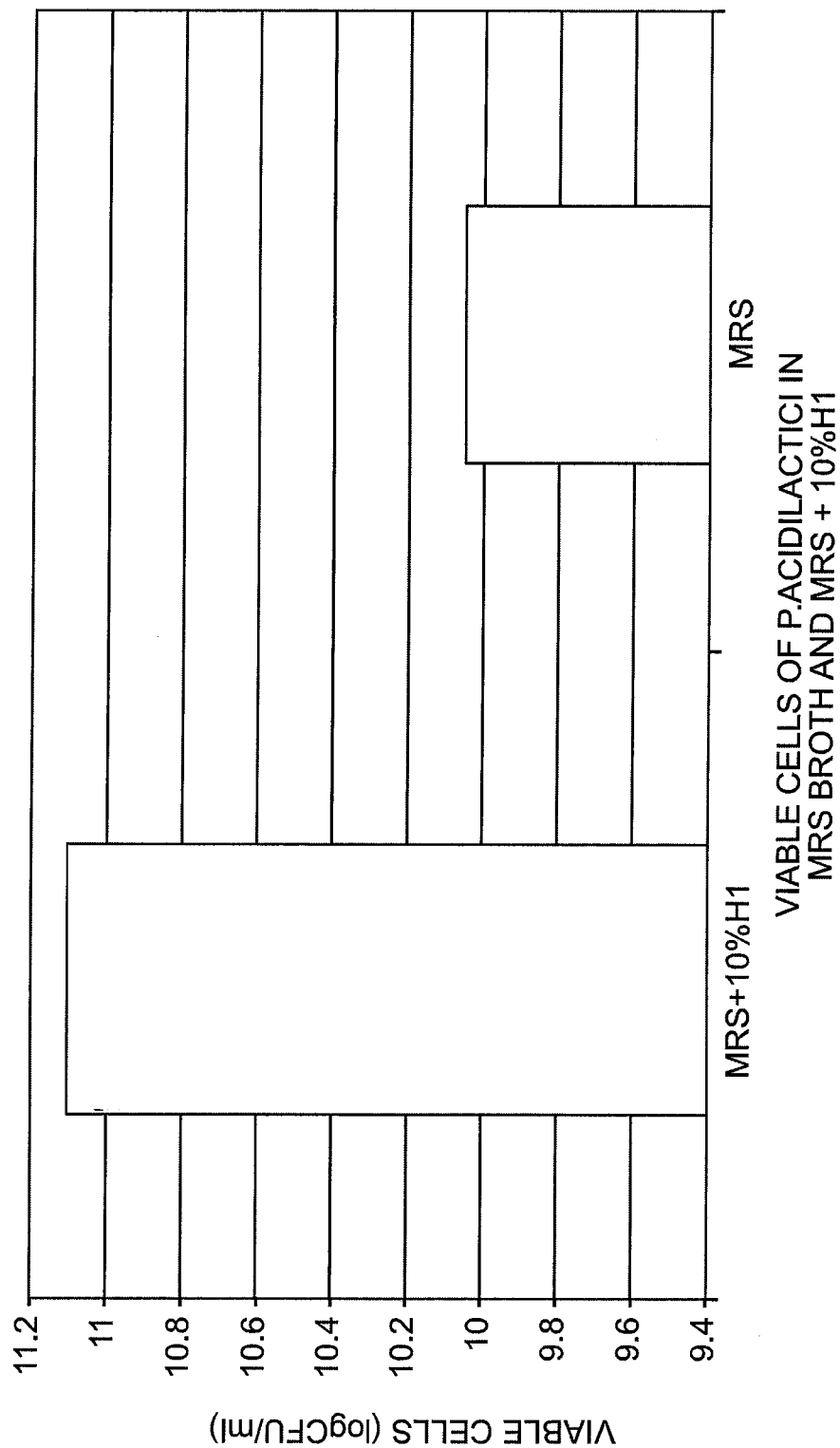
FIG. 2: Viable cells of *P. acidilactici* in MRS broth and MRS+10% TLBH; MRS+10% H1=a 90:10 MRS:TLBH mixture v/v; MRS=MRS control.
Figure 3:
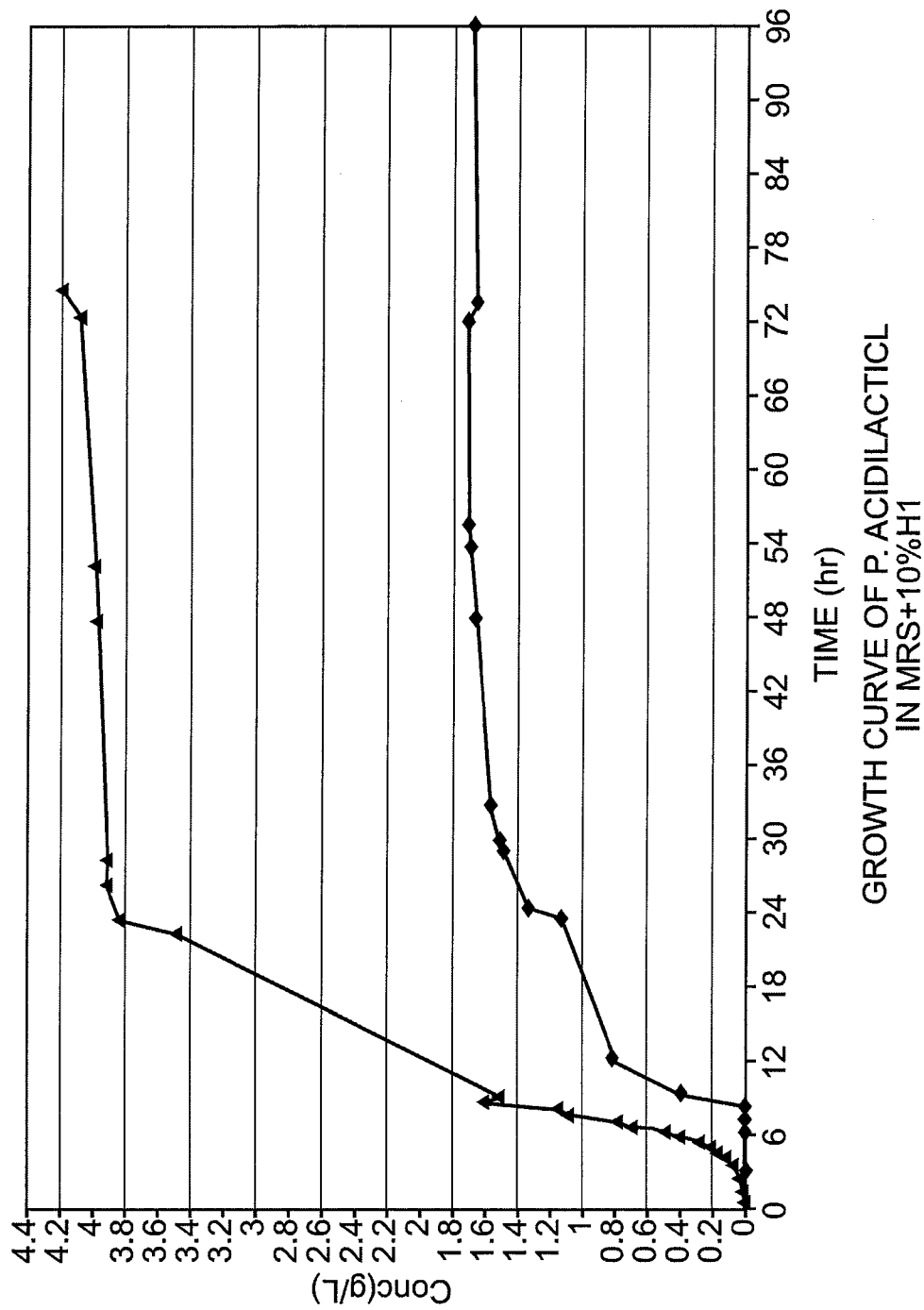
FIG. 3: Growth comparison of *P. acidilactici* grown in MRS (bottom) and 10% TLBH solution in MRS (top line).

The sample containing 10% TLBH showed a dramatic yield increase, producing in excess of ten times the colony forming units as the MRS control (FIG. 2). The TLBH sample also had a substantially shortened lag phase and entered the exponential phase approximately three hours earlier than in the MRS control (FIG. 3).

Example 3

Production of Organic Acids

The inventors found that LBH when used as a substrate rapidly produces large volumes of organic acids. The inventors found a dramatic increase in the concentration of several organic acids during anaerobic fermentation conditions when the lactic acid bacterial species P. acidilactici was given a TLBH substrate prepared using the method of Example 2 above, including lactic acid, propionic acid and acetic acid. This result indicates that LBH is a useful substrate in the production of organic acids. For all three organic acids analyzed, these results indicated that the P. acidilactici cells were utilizing the growth medium containing LBH metabolically.

The results for lactic acid production are particularly noteworthy and unexpected. Commercial production of lactic acid using bacterial fermentation is limited due to the difficulties and expense of culturing lactic acid-producing bacteria under anaerobic conditions. The fact that a lactic acid-producing bacterial species was able to thrive under anaerobic conditions with an LBH substrate is strong evidence that LBH is a suitable substrate for the commercial production using fermentation of lactic acid.

Organic Acid Analysis

Organic acids were analyzed using an HPLC-apparatus consisting of an Aminex HPX-87H column. As the mobile phase 0.0125M sulphuric acid was used at a flow rate of 0.6 ml/min. The separation temperature was kept at 60° C. The UV detector was used at 210 nm.

After centrifuging at 4000 rpm for 10 min, the supernatant was carefully taken off with clean pipette, and a dilution of 1:5-1:10 were made with DI water. The samples were submitted to Carrez-Precipitation to separate and precipitate the disturbing protein in order to facilitate the extraction of organic acids.

Lactic Acid: Lactic acid was initially present in TLBH at the very low concentration of 0.0212 g/l. Within a 24 hr fermentation, it reached a concentration of 2.9845 grams per liter. This represents a 140-fold increase in lactic acid concentration within 24 hours. Concentrations of lactic acid then remained essentially stable for the next 29 days (FIG. 4).

The proportionate increase in lactic acid concentration compares favorably with other results contained in the literature. For example, Kious (2000) found only a 10-fold increase in lactic acid concentration over 22 hours and a 12-fold increase over 30.5 hours using a specially selected Lactobacillus strain of bacteria fermenting at 37° C. and providing a substrate containing 10% glucose.

Propionic Acid. The initial concentration of propionic acid in TLBH was 0.0305 g/l. After 24 hrs fermentation using P. acidilactici bacteria, the concentration of propionic acid increased to 0.938 grams/l. This represented more than a 30-fold increase in concentration of propionic acid. Propionic acid is useful as a preservative. Our results indicate that TLBH is useful as a substrate in the production of propionic acid.

Acetic Acid. The initial concentration of acetic acid in TLBH was 0.262 g/l. After 24 hrs fermentation using P. acidilactici, the concentration of acetic acid increased to 0.934 g/l. This represents 3.5-fold increase in production.

Acetic acid is widely used in acidulants and antimicrobials. It is also used as a chemical reagent for the production of chemicals. Although a small portion of acetic acid is presently produced through fermentation, the overwhelming majority of current acetic acid production is through synthetic means. Our data indicates that TLBH could be used as a substrate to increase fermentation-based production of acetic acid.

Example 5

Effect of TLBH on E. coli growth (FIG. 5)

We compared the effectiveness of TLBH in promoting the growth of E. coli bacteria against a standard growth medium suitable for E. coli production. This experiment included two treatments:

(a) TSB+TLBH. This treatment consisted of a mixture containing 20 ml of TLBH plus 80 ml of tryptic soy broth (TSB), a standard commercial growth medium suitable for E. coli production (i.e., an 80:20 TSB:TLBH treatment)

(b) TLBH+Glucose+Soy meal+TSB. The purpose of this treatment was to evaluate whether TLBH could stimulate the growth of E. coli in conjunction with low cost substrates such as glucose and soy meal and only minimal quantities of commercial growth media. This treatment consisted of 20 ml TLBH+0.5 ml+2 ml soy meal+3.25 ml TSB, with the remainder of the 100 ml mixture made up of distilled water.

(c) This test also included a control containing 100 ml of TSB. In this test, the E. coli type was ATCC 25922. The glucose was dextrose from corn sugar, obtained from SIGMA. The soy meal was Southern States Soybean Meal Hi-Pro (47.5% minimum crude protein 0.7% minimum crude fat, and 3.6% maximum crude fiber). The TSB was Bacto™ Tryptic Soy Broth(DIFCO).

The TSB+TLBH treatment proved superior to the TSB control. (Data presented is after four (4) hours, when the bacteria entered a stable phase). The viable cell count for the TSB+TLBH treatment was nearly $10^{9.7}$ CFU/ml. By contrast, the cell count for the TSB control was just under $10^{9.5}$ CFU/ml. This data demonstrates that the addition of TLBH to a commercial growth medium was able to stimulate growth of E. coli more effectively than a treatment consisting solely of the commercial medium.

The treatment containing glucose and soy meal performed less well than the control, with a four hour cell count of about $10^{9.15}$ CFU/ml. Nonetheless, this result still surpassed the threshold described by Heenan's (2002), that an ideal medium should be able to promote growth of up to $10^9$ CFU/ml. This result demonstrates that TLBH in conjunction with low-cost substrates and a minimal amount of commercial medium was able to promote acceptable growth of E. coli. It indicates that TLBH and LBH could be utilized in fermentation processes in conjunction with low-cost substrates with little or no supplementation of commercial growth media.

Example 6

E. coli Colonization on a TLBH substrate

We found that TLBH stimulated the growth of a generic, non-pathogenic strain of E. coli bacteria, when compared with the standard bacterial growth medium MRS. One (1) ml of E. coli was harvested in 9 ml Luria broth for 24 hours. A ten-fold dilution of the bacteria was prepared, and then 0.1 ml of the bacteria was added to each of two petri plates. One plate contained agar to which TLBH (prior to drying down) had been added. The second plate contained an agar to which about 20 ml of MRS had been added. The plates were then incubated at 37° C. for 48 hours.

We found that E. coli colonies were able to establish on the plate treated with TLBH and agar. However, bacterial colonies did not establish on the MRS-agar plate. This result indicated that TLBH stimulates the growth of E. coli bacterial cells.

E. coli is one of the most widely used microbial species in the production of ethanol and other biofuels and industrial fermentations. Our ability to establish colonies of non-pathogenic E. coli using LBH from tobacco biomass is evidence that LBH is a useful substrate in the production of biofuels and industrial fermentations.

Example 7

Chemical Analysis of TLBH

The inventors performed an analysis of dried, powdered TLBH for sugars and oligosaccharides and found that it contained the following constituents:

| Content (mg/100 g dried powdered leaf) | LBH |
|---|---|
| Glucose | 0.3/1.04* |
| Fructose | 0.08/0.72* |
| Sucrose | 0.8 |
| Fructooligosaccharides (FOS) | 0.55 |

*The first value for glucose and fructose indicates the initial presence of that sugar, the second value indicates the presence of that sugar after the TLBH was treated with the oligosaccharide-digesting enzyme inulinase.

A vitamin analyses of TLBH determined that it contains traces of vitamins that promulgate the growth of microbial species: thiamine (vitamin B1), pantothenic acid (vitamin B5), folic acid (vitamin B9) and biotin (vitamin H). The presence of these necessary trace components may help to explain why use of TLBH as a substrate has produced strong microbial growth. It is also evidence that TLBH can be used in conjunction with inexpensive protein and carbohydrates sources to produce compounds and materials which would otherwise require use of complex and expensive substrates for fermentation-based production.

Example 8

Effectiveness of leaf biomass hydrolysate method using species other than tobacco.

The purpose of this experiment was to determine whether our leaf biomass hydrolysate method was effective with species other than tobacco. We selected spinach and alfalfa as our test species, since like tobacco, they are species rich in leaf proteins. The alfalfa was of variety UMN 3988, biomass 1 germplasm cycle 2, a selection for woody stems for non-lodging, harvested in the vegetative state (provided by U.S. Department of Agriculture, Agricultural Research Service, St. Paul, Minn.). Spinach was store-purchased fresh green spinach leaves which had been refrigerated prior to purchase. TLBH was also utilized.

For tobacco, the inventors utilized the source material and method of treatment 4 of Example 1 above to remove the green juice and select the biomass fraction for preparation of tobacco leaf biomass hydrolysate (TLBH). For both alfalfa and spinach, leaves were cleaned by running under tap water for about 15 minutes. Leaves were then oven-dried at a temperature between 45-50° C. for 40 hours.

For all three treatments, dried leaves (10 g) were placed in a 250 ml beaker containing 150 ml distilled water and heated in a water bath at 75° to 80° C. for two hours. The hydrolysates were then filtered through a Whatman No. 4 filter paper. The hydrolysates were then stored at −16° C. until use.

A control was established in which MRS agar alone was used as a growth medium for P. acidilactici. For each of the three biomass hydrolysate treatments, 20% of the MRS agar was replaced with LBH derived from one of the plant species respectively. Results of this test are reported in FIG. 6. They represent bacterial count at 12 hours, when the bacteria entered a stable growth phase.

All three of the experimental treatments resulted in enhanced growth of P. acidilactici, compared to the control. The TLBH treatment gave the highest yields, at over $10^{12}$ CFU/ml. However, the spinach and alfalfa treatments were also clearly more effective than the control. These results indicate that a wide variety of species of plant leaves may be used to produce growth enhancing LBH. Persons skilled in the art will be able to determine which plant species will produce an LBH optimized for their own specific needs with from knowledge common in the field and minimal experimentation.

While the foregoing invention has been described in some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

What is claimed is:

1. A growth medium comprising a tobacco leaf biomass hydrolysate (TLBH) wherein TLBH is a product produced from the following steps in the following chronological order:
   (a) disrupting one or more tobacco leaves;
   (b) sterilizing by drying the disrupted leaves to a water activity level of approximately 0.85 or lower
   (c) incubating the disrupted leaves in a liquid wherein incubating comprises heating the disrupted leaves in water to a temperature of from about 60° C. to about 90° C. for a period of time of ranging from about 15 minutes to about one (1) week;
   (d) filtering the liquid after incubation to remove solids, and produce a liquid comprising soluble constituents of TLBH; and
   (e) placing the soluble constituents of TLBH resulting from the filtering step of (d) into a growth medium.

2. A growth medium according to claim 1, wherein the growth medium is a powder.

3. A growth medium according to claim 1, wherein the growth medium is a prokaryotic growth medium.

4. A growth medium according to claim 1, wherein the growth medium is a eukaryotic growth medium.

5. A growth medium according to claim 1, wherein at least one desirable leaf component is removed from the leaves, during or after the leaves are disrupted.

6. A growth medium according to claim 1, wherein the filtered liquid of step (d) is dried to a powder prior to being placed into a growth medium.

7. A growth medium according to claim 1, wherein the dried, disrupted leaves of step (b) are packaged in filter paper, ground into a powder and packaged, or packaged as disrupted leaves without either filter paper or being ground into a powder, prior to performing the incubating of step (c).

* * * * *